US011567058B2

United States Patent
Shi et al.

(10) Patent No.: US 11,567,058 B2
(45) Date of Patent: Jan. 31, 2023

(54) PROCESS FOR OPTIMIZED CHEMICAL ENHANCED RECOVERY

(71) Applicant: Chevron U.S.A. Inc., San Ramon, CA (US)

(72) Inventors: Xundan Shi, Houston, TX (US); Choongyong Han, Houston, TX (US); Yih-Bor Chang, Houston, TX (US); Christian Wolfsteiner, Houston, TX (US); Baris Guyaguler, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 188 days.

(21) Appl. No.: 16/138,625

(22) Filed: Sep. 21, 2018

(65) Prior Publication Data
US 2019/0094199 A1 Mar. 28, 2019

Related U.S. Application Data (60) Provisional application No. 62/561,929, filed on Sep. 22, 2017.

(51) Int. Cl.
*G06F 17/11* (2006.01)
*G01N 33/28* (2006.01)
(Continued)

(52) U.S. Cl.
CPC ....... *G01N 33/2823* (2013.01); *E21B 43/162* (2013.01); *G01V 99/005* (2013.01); *G06F 17/11* (2013.01)

(58) Field of Classification Search
CPC .............. G01N 33/2823; E21B 43/162; G01V 99/005; G06F 17/11
See application file for complete search history.

(56) References Cited

U.S. PATENT DOCUMENTS 4,258,789 A * 3/1981 Hedges ................... B01F 17/00
166/252.3
4,856,589 A * 8/1989 Kuhlman .............. E21B 43/164
507/938
(Continued)

FOREIGN PATENT DOCUMENTS

WO 2016126759 A1 8/2016

OTHER PUBLICATIONS

Extended European Search Report dated Nov. 2, 150108 in corresponding EP Application No. 18196077.4.
(Continued)

*Primary Examiner* — Ashish Thomas
*Assistant Examiner* — Nargis Sultana
(74) *Attorney, Agent, or Firm* — William N. Hughet; Ana Cristina Jaquez; Melissa M. Hayworth (57) ABSTRACT

A method for simulating a microemulsion system in a chemical enhanced oil recovery process is disclosed. The method includes receiving a geological model of a subsurface reservoir that defines a grid having a plurality of cells, determining a surfactant concentration for each cell based on a volume of surfactant and a volume of water within the cell and independently from a volume of oil in the cell, and simulating fluids flowing in the subsurface reservoir. Results from simulation can be used to optimize a chemical enhanced oil recovery process in a subsurface reservoir.

20 Claims, 7 Drawing Sheets

(51) Int. Cl.
*E21B 43/16* (2006.01)
*G01V 99/00* (2009.01)

(56) References Cited

U.S. PATENT DOCUMENTS

| | | | |
|---|---|---|---|
| 6,460,622 B1* | 10/2002 | Rice | F04B 49/065 |
| | | | 417/36 |
| 8,235,117 B1* | 8/2012 | Hill | E21B 43/247 |
| | | | 166/303 |
| 10,119,374 B2 | 11/2018 | Patacchini et al. | |
| 2006/0129341 A1* | 6/2006 | Beetge | G01N 33/2847 |
| | | | 702/65 |
| 2007/0294034 A1* | 12/2007 | Bratton | E21B 43/00 |
| | | | 702/6 |
| 2009/0070085 A1* | 3/2009 | Gullapalli | G06F 30/20 |
| | | | 703/12 |
| 2012/0232859 A1* | 9/2012 | Pomerantz | G01V 1/282 |
| | | | 703/2 |
| 2012/0292025 A1* | 11/2012 | Stoll | E21B 43/16 |
| | | | 166/269 |
| 2014/0202927 A1* | 7/2014 | Tao | B01D 17/047 |
| | | | 208/188 |
| 2014/0305649 A1* | 10/2014 | Tang | C09K 8/602 |
| | | | 166/308.2 |
| 2015/0073762 A1* | 3/2015 | Patacchini | E21B 43/16 |
| | | | 703/10 |
| 2015/0100293 A1* | 4/2015 | Hoteit | E21B 43/16 |
| | | | 703/10 |
| 2016/0319640 A1* | 11/2016 | Ratulowski | E21B 41/00 |
| 2016/0340568 A1* | 11/2016 | Natali | E21B 49/08 |
| 2016/0341037 A1* | 11/2016 | Natali | G06Q 50/00 |
| 2016/0356142 A1* | 12/2016 | Natali | E21B 21/068 |
| 2017/0234121 A1* | 8/2017 | Anisur Rahman | E21B 43/20 |
| | | | 166/250.07 |
| 2018/0032356 A1* | 2/2018 | Su | E21B 43/20 |
| 2018/0066515 A1* | 3/2018 | Balan | E21B 34/06 |
| 2018/0107768 A1* | 4/2018 | Shaykhattarov | G06F 17/13 |
| 2018/0283149 A1* | 10/2018 | Vittoratos | E21B 43/20 |
| 2018/0371873 A1* | 12/2018 | Bhatnagar | E21B 43/26 |
| 2019/0225870 A1* | 7/2019 | Johns | G01N 33/2823 |

OTHER PUBLICATIONS

Acosta, E., et al., "Net-Average Curvature Model for Solubilization and Supersulubilization in Surfactant Microemulsions", Langmuir (2003) 19:186-195.

Fuseni, Alhasan B., et al., "Critical Micelle Concentration of Different Classes of EOR Surfactants under Representative Field Conditions", SPE-188011-MS, Kingdom of Saudi Arabia Annual Technical Symposium and Exhibition held in Damman, Saudi Arabia Apr. 24-27, 2017; pp. 1-8.

Ghosh, Soumyadeep and Russell T. Johns, "Dimensionless Equation of State to Predict Microemulsion Phase Behavior", Langmuir (2016) 32:8969-8979.

Han, Choongyong, et al., "A New Four-Phase Flash Algorithm for Surfactant Flood Simulation", SPE-182653-MS, Reservoir Simulation Conference, Montgomery, TX, Feb. 20-22, 2017; pp. 1-20.

Jin, Luchao, et al., "Physics based HLD-NAC phase behavior model for surfactant/crude oil/brine systems", J. Petroleum Science and Engineering, (2015) 136:68-77.

Khorsandi, Saeid and Russell T. Johns, "Robust Flash Calculatin Algorithm for Microemulsion Phase", J. Surfact Deterg., (2016) 19:127301287.

Noll, L.A., "The Effect of Temperature, Salinity, and Alcohol on the Critical Micelle Concentration of Surfactants", SPE 21032, International Symposium on Oilfield Chemistry, Anaheim, CA, Feb. 20-22, 1991; pp. 1-7.

Mouraei, Mehdi and Edgar J. Acosta, "Predicting solubilisation features of ternary phase diagrams of fully dilutable lecithin linker microemulsions", Journal of Colloid and Interface Science (2017) 495:178-190.

Shi, Xundan, et al., "A Mixed Natural and Concentration Variable Formulation for Chemical Flood Simulation", SPE-182703-MS Reservoir Simulation Conference, Montgomery, TX Feb. 20-22, 2017; pp. 1-16.

Patacchini, L., et al., "Four-Fluid-Phase, Fully Implicit Simulation of Surfactant Flooding", SPE Reservoir Evaluation & Engineering, 2014, pp. 271-285.

* cited by examiner

PROCESS FOR OPTIMIZED CHEMICAL ENHANCED RECOVERY

CROSS-REFERENCE TO RELATED APPLICATIONS

The present application claims priority from U.S. Provisional Patent Application No. 62/561,929, filed on Sep. 22, 2017, the disclosure of which is hereby incorporated by reference in its entirety.

TECHNICAL FIELD

The present disclosure relates generally to a method for simulating fluid flow in a subsurface reservoir and forecasting oil recovery from the subsurface reservoir using a chemical enhanced oil recovery process. In particular, the present disclosure relates to simulation of microemulsion systems in chemical enhanced oil recovery processes and eliminating unphysical solutions in chemical enhanced oil recovery simulations produced via calculation of cell surfactant concentration which is used to compare with critical micelle concentration (CMC). The present disclosure further relates generally to performing a chemical enhanced oil recovery process according to chemical enhanced oil recovery simulations.

BACKGROUND

One technique for recovering oil or hydrocarbons from a hydrocarbon-bearing formation involves chemical enhanced oil recovery processes. In chemical enhanced oil recovery processes, a chemical solution (i.e., an injection fluid including at least one surfactant, co-surfactant, alkali, or co-solvent) is injected into a subsurface oil reservoir. For example, in surfactant flooding processes, surfactant mixes with the oil and water present in the reservoir forming microemulsion systems having one or more fluid phases. Various types of microemulsion systems may form having a microemulsion of oil, water (or brine), and surfactant. In particular, a single-phase system, two-phase systems, or a three-phase system are possible. The single-phase system includes a microemulsion phase. The two-phase system can include a microemulsion phase and an excess oil phase. Alternatively, the two-phase system can include a microemulsion phase and an excess aqueous phase. The three-phase system includes a microemulsion phase, an excess oil phase, and an excess aqueous phase.

The number of phases formed, and the composition(s) of the phases vary depending upon variables associated with the microemulsion system, for example, the salinity, the surfactant concentration, temperature, and pressure. It is desirable to model microemulsions in chemical enhanced oil recovery processes in reservoir simulations to accurately simulate fluid flow and forecast field scale oil recovery.

Identification of where microemulsion systems reside in the subsurface reservoir at each time step during fluid flow simulation is a critical component for modeling microemulsion systems in chemical enhanced oil recovery simulations. Typically, reservoir simulators allow for construction of a grid or mesh to discretize the subsurface reservoir model. The grids are generally composed of a plurality of cells that are associated with various rock and fluid properties of the subsurface reservoir. One skilled in the art will recognize that various approaches can be used for generating grids or meshes. U.S. patent application Ser. No. 14/049,877 (filed on 9 Oct. 2013), titled "Method for Efficient Dynamic Gridding," discloses an exemplary method for generating grids for use in reservoir simulations, which is incorporated herein by reference.

Once a grid is constructed, cells can be labeled as having a micro-emulsion phase when a cell's surfactant concentration reaches a predetermined amount (e.g., greater than a lab measured critical micelle concentration (CMC) for the chemical solution being injected into the reservoir). To determine when a cell's surfactant concentration reaches a predetermined amount, a surfactant concentration must be calculated for each cell. A widely-adopted definition for surfactant concentration used in reservoir simulators is given as:

$$SC = \frac{V_{surfactant}}{V_{oil} + V_{surfactant} + V_{water}} \quad (1)$$

where $V_{surfactant}$, $V_{oil}$, and $V_{water}$ represent volumes of surfactant, oil and water components, respectively. Thus, the surfactant concentration is equivalent to a volume of surfactant component divided by a sum of a volume of oil component, a volume of surfactant component, and a volume of water component. If the cell's surfactant concentration is greater than lab-measured CMC for the surfactant used, then the cell would be labeled as having a microemulsion phase; otherwise, no microemulsion phase exists in the cell.

For cases where water mobility is greater than oil mobility, an oil bank tends to form near the injection front. Accordingly, oil volumes increase while surfactant and water volumes decrease within cells near the injection front. Based on the above SC definition in equation (1), this can make surfactant concentration near the injection front where the oil bank forms fall below the CMC, which results in the disappearance of the micro-emulsion phase. If in some cells, the surfactant concentration is above CMC and in neighboring cells the surfactant concentration is below CMC, the simulation solution exhibits a checkerboard pattern in micro-emulsion phase distribution. The checkerboard pattern is an unphysical solution (not what is actually happening in the physical system) due to the definition from Equation (1) (e.g., domination of the $V_{oil}$ component).

Figure 1:
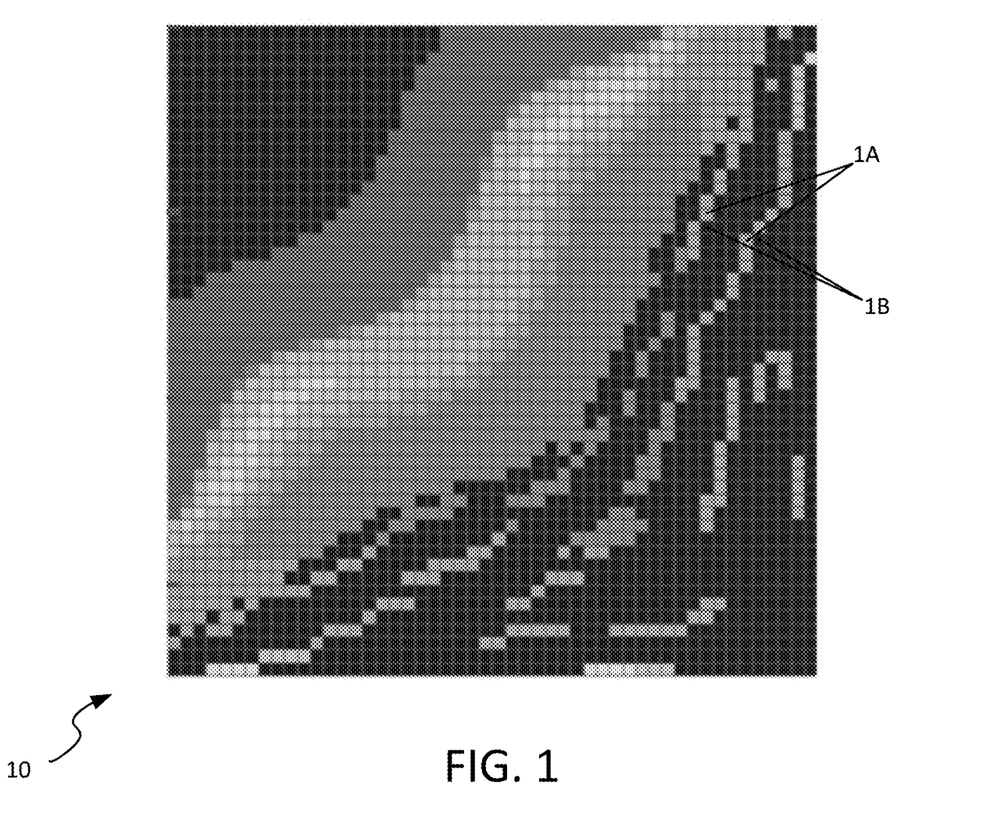
FIG. 1 provides a micro-emulsion phase saturation diagram produced during simulation of a chemical enhanced oil recovery process in a subsurface oil reservoir.

FIG. 1 is a diagram showing a user interface 10 in which micro-emulsion phase saturation is shown from simulation for a typical chemical injection during an enhanced oil recovery project (e.g., surfactant flooding). In FIG. 1, a checkerboard pattern is exhibited near the injection front. In particular, some cells 1A in the simulation grid that are shaded in a lighter color exhibit a microemulsion phase while neighboring or adjacent cells 1B that are shaded in a darker color are shown not having a microemulsion phase. This numerical solution is unphysical because the surfactant concentration calculated for cells 1B in equation (1) falls below a predetermined threshold value (e.g., lab measured critical micelle concentration (CMC) that is input into the simulator). For example, the predetermined threshold value, such as a lab measured critical micelle concentration (CMC), can be entered into the reservoir simulator as a constant parameter value (e.g., $10^{-4}$).

Accordingly, there is a need for an improved method of predicting and simulating microemulsions in chemical enhanced oil recovery processes such that unphysical solutions are eliminated in chemical enhanced oil recovery simulations.

SUMMARY

In accordance with the following disclosure, the above and other issues are addressed by the following:

In a first aspect, a method for simulating a microemulsion system in a chemical enhanced oil recovery process is disclosed. The method includes receiving a geological model of a subsurface reservoir, the geological model defining a grid having a plurality of cells. The method further includes determining a surfactant concentration for each cell based on a volume of surfactant and a volume of water within the cell and independently from a volume of oil within the cell. The method also includes simulating fluids flowing in the subsurface reservoir.

In a second aspect, a system for simulating a microemulsion system in a chemical enhanced oil recovery process is disclosed. The system includes a memory communicatively connected to a processing unit. The memory stores instructions which, when executed by the processing unit, cause the system to simulate a microemulsion system in a chemical enhanced oil recovery process. The instructions cause the system to perform: receiving a geological model of a subsurface reservoir, the geological model defining a grid having a plurality of cells; determining a surfactant concentration for each cell based on a volume of surfactant and a volume of water within the cell and independently from a volume of oil within the cell; and simulating fluids flowing in the subsurface reservoir using the critical micelle concentration for each cell.

In some aspects, the determination of surfactant concentration is based only on a volume of surfactant and volume of water within the cell. In further aspects, simulating fluids flowing in the subsurface reservoir includes generating a visual representation of the plurality of cells that eliminates one or more simulation artifacts that represent unphysical solutions occurring during simulation of a chemical enhanced oil recovery process. In still further aspects, the methods and systems utilized adjust, in response to the simulated fluid flow, one or more oil recovery parameters used in performing the chemical enhanced oil recovery process.

DETAILED DESCRIPTION

In the following detailed description, reference is made to the accompanying drawings showing by way of illustration specific embodiments of methods and systems disclosed herein. It is to be understood that other embodiments may be utilized and logical changes may be made without departing from the scope of the present disclosure. The following detailed description, therefore, is not to be taken in a limiting sense.

As briefly described above, methods and systems for simulating a microemulsion system in a chemical enhanced oil recovery process are disclosed. The methods and systems described herein determine surfactant concentration for each cell based on a volume of surfactant and a volume of water within the cell. In some instances, this surfactant concentration determination occurs without regard to, or at least with insignificant effect from a volume of oil within the cell, to avoid unphysical effects appearing in the simulation. In particular instances, only the volume of surfactant and the volume of water are considered.

The simulation system of the present disclosure has a number of advantages. For example, by primarily utilizing volume of surfactant and volume of water within a cell to determine surfactant concentration, unphysical solutions that appear in simulation due to the volume of oil included in the model can be avoided. This allows a user of the simulation to more accurately adjust production parameters, and provides a simulation with significantly improved accuracy in terms of reflecting actual conditions within an oil recovery process.

In accordance with the present disclosure, certain terminology as used in this disclosure is provided below, followed by a description of methods and systems for performing such a simulation and adjusting a chemical enhanced oil recovery process in response to such improved simulation(s).

TERMINOLOGY: The following terms will be used throughout this disclosure and will have the following meanings unless otherwise indicated:

The term "brine" as used herein refers to an aqueous solution of salts and other water soluble compounds. The term "water" is used interchangeably with the term "brine" herein.

Hydrocarbon-bearing formation: Hydrocarbon exploration processes, hydrocarbon recovery processes, or any combination thereof may be performed on a "hydrocarbon-bearing formation". The hydrocarbon-bearing formation refers to practically anything under a surface. For example, the hydrocarbon-bearing formation may be practically anything under a terrestrial surface (e.g., a land surface), practically anything under a seafloor, etc. A water column may be above the hydrocarbon-bearing formation, such as in marine hydrocarbon exploration, in marine hydrocarbon recovery, etc. The hydrocarbon-bearing formation may be onshore in some embodiments. Alternatively, the hydrocarbon-bearing formation may be offshore, with shallow water or deep water above the hydrocarbon-bearing formation, in some embodiments. The hydrocarbon-bearing formation may include faults, fractures, overburdens, underburdens, salts, salt welds, rocks, sands, sediments, pore space, etc. The hydrocarbon-bearing formation may include practically any geologic point(s) or volume(s) of interest (such as a survey area) in some embodiments.

The hydrocarbon-bearing formation may also include hydrocarbons, such as liquid hydrocarbons (also known as oil or petroleum). Light crude oil, medium oil, heavy crude oil, and extra heavy oil, as defined by the American Petroleum Institute (API) gravity, are examples of hydrocarbons.

The hydrocarbon-bearing formation may also include at least one wellbore. For example, at least one wellbore may be drilled into the hydrocarbon-bearing formation in order to confirm the presence of the hydrocarbons. As another example, at least one wellbore may be drilled into the hydrocarbon-bearing formation in order to recover the hydrocarbons. The hydrocarbons may be recovered from the entire hydrocarbon-bearing formation or from a portion of the hydrocarbon-bearing formation. For example, the hydrocarbon-bearing formation may be divided up into one or more hydrocarbon zones, and hydrocarbons may be recovered from each desired hydrocarbon zone. One or more of hydrocarbon zones may even be shut-in to increase hydrocarbon recovery from a hydrocarbon zone that is not shut-in.

The hydrocarbon-bearing formation, the hydrocarbons, or any combination thereof may also include non-hydrocarbon items. For example, the non-hydrocarbon items may include connate water, brine, tracers, items used in enhanced oil recovery or other hydrocarbon recovery processes, items from other treatments (e.g., gels used in conformance control), etc.

In short, each hydrocarbon-bearing formation may have a variety of characteristics, such as petrophysical rock properties, reservoir fluid properties, reservoir conditions, hydrocarbon properties, or any combination thereof. For example, each hydrocarbon-bearing formation (or even zone or portion of the hydrocarbon-bearing formation) may be associated with one or more of: temperature, porosity, permeability, water composition, mineralogy, hydrocarbon type, hydrocarbon quantity, reservoir location, pressure, etc. Those of ordinary skill in the art will appreciate that the characteristics are many, including, but not limited to: shale gas, shale oil, tight gas, tight oil, tight carbonate, carbonate, vuggy carbonate, unconventional (e.g., a rock matrix with an average pore size less than 1 micrometer), diatomite, geothermal, coalbed methane, hydrate, mineral, metal, a hydrocarbon-bearing formation having a permeability in the range of 0.01 microdarcy to 10 millidarcy, a hydrocarbon-bearing formation having a permeability in the range of 10 millidarcy to 40,000 millidarcy, etc.

The term "hydrocarbon-bearing formation" may be used synonymously with the term "reservoir" or "subsurface reservoir" or "subsurface region of interest" or "formation" or "subsurface formation" or "subsurface volume of interest". Thus, the terms "hydrocarbon-bearing formation," "hydrocarbons," and the like are not limited to any description or configuration described herein.

Hydrocarbons may be recovered from the formation using enhanced oil recovery. The term "enhanced oil recovery" refers to techniques for increasing the amount of hydrocarbons that may be extracted from the formation. This disclosure utilizes chemical enhanced oil recovery processes for hydrocarbon recovery. As used herein, chemical enhanced oil recovery (CEOR) processes refers to injection of a chemical solution. For example, CEOR can include polymer flooding, alkaline flooding, surfactant flooding, conformance control operations, as well as combinations thereof such as alkaline-polymer (AP) flooding, surfactant-polymer (SP) flooding, or alkaline-surfactant-polymer (ASP) flooding.

EOR processes include, for example: (a) miscible gas injection (which includes, for example, carbon dioxide flooding), (b) chemical injection (sometimes referred to as chemical enhanced oil recovery (CEOR) that includes, for example, polymer flooding, alkaline flooding, surfactant flooding, conformance control, as well as combinations thereof such as alkaline-polymer flooding, surfactant-polymer flooding, or alkaline-surfactant-polymer flooding), (c) microbial injection, (d) thermal recovery (which includes, for example, cyclic steam and steam flooding), or any combination thereof. As an example, a CEOR process may include practically any flooding involving polymer, a chemical agent, or any combination thereof. For example, the CEOR process may comprise a polymer (P) flooding process, an alkaline-polymer (AP) flooding process, a surfactant-polymer (SP) flooding process, an alkaline-surfactant-polymer (ASP) flooding process, or any combination thereof.

Chemical enhanced oil recovery includes all EOR processes (e.g., drive, push-pull) and all phases of the reservoir life. For example, the general procedure of a chemical flood includes a pre-flush (e.g., low-salinity water) to condition the reservoir, injection of the chemical solution, a buffer solution (e.g., thickened water) to protect the pH of the chemical solution and/or to improve sweep efficiency, and a drive fluid (e.g., produced brine), which displaces the chemicals and resulting hydrocarbon bank to adjacent production wells. The terms "operation" and "application" may be used interchangeability herein, as in EOR operations or EOR applications.

Turning to the CEOR process, the polymer can be initially provided as a powder that is mixed on-site, or the polymer can be initially provided in a partial-strength solution, such as gel, emulsion, or liquid that is made up partly of polymer (e.g., 2%-60% polymer) in a solute such as water. An injection fluid may be mixed on-site to include the polymer, e.g., by mixing the polymer (that may have been initially provided as a powder, gel, emulsion, or liquid) with a solute such as water. Preparing the powder polymer may involve at least one additional mixing step and storage of the result in a tank (e.g., tank on the surface). The result from the tank is then mixed with the solute to form the injection fluid. The injection fluid may also include other components in addition to the polymer.

In one embodiment, an injection fluid may include a variety of components. For example, the injection fluid may include (i) a water or aqueous phase component, such as brine, a mixture of brine and gas, etc. The injection fluid may include (ii) a polymer component, and the polymer component may include various constituents such as water, mineral oil, one or more solvents, one or more optional additives, etc. The polymer component may include additional and/or alternative constituents as well. The injection fluid may include (iii) a solids component, such as sands, other solids, etc. The injection fluid may also include (iv) a fourth component, such as one or more solvents, one or more optional additives, etc. The fourth component may include additional and/or alternative constituents as well. For example, the polymer component may include surfactant and the fourth component may also include surfactant. The injection fluid may include additional components as well, for example, that may be mixed on-site. Thus, the injection fluid may include a variety of components, and the actual components of the injection fluid may depend, for example, on the hydrocarbon-bearing formation and the hydrocarbons.

"Wellbore" refers to a single hole for use in hydrocarbon recovery, including any openhole or uncased portion of the wellbore. For example, a wellbore may be a cylindrical hole drilled into the formation such that the wellbore is surrounded by the formation, including rocks, sands, sediments, etc. A wellbore may be used for injection. A wellbore may be used for production. In some embodiments, a single injection wellbore may have at least one corresponding production wellbore, and the hydrocarbons are swept from the single injection wellbore towards the at least one corresponding production wellbore and then up towards the surface.

The wellbore may include a casing, a liner, a tubing string, a wellhead, a sensor, etc. The "casing" refers to a steel pipe cemented in place during the wellbore construction process to stabilize the wellbore. The "liner" refers to any string of casing in which the top does not extend to the surface but instead is suspended from inside the previous casing. The "tubing string" or simply "tubing" is made up of a plurality of tubulars (e.g., tubing, tubing joints, pup joints, etc.) connected together and it suitable for being lowered into the casing or the liner for injecting a fluid into the formation, producing a fluid from the formation, or any combination thereof. The casing may be cemented into the wellbore with the cement placed in the annulus between the formation and the outside of the casing. The tubing string and the liner are typically not cemented in the wellbore. The wellbore may include an openhole portion or uncased portion. The wellbore may include any completion hardware that is not discussed separately. The wellbore may have vertical, inclined, horizontal, or combination trajectories. For example, the wellbore may be a vertical wellbore, a horizontal wellbore, a multilateral wellbore, or slanted wellbore. The term wellbore is not limited to any description or configuration described herein. The term wellbore may be used synonymously with the terms borehole or well.

The wellbore may be used for injection in some embodiments. The wellbore may be used for production in some embodiments. The wellbore may be used for fracturing in some embodiments. The wellbore may be used for a single function, such as only injection, in some embodiments. The wellbore may be used for a plurality of functions, such as both injection and production (e.g., cyclic steam also referred to as steam soak), in some embodiments. The use of the wellbore may also be changed, for example, a particular wellbore may be turned into an injection wellbore after a different previous use. The wellbore may be new or pre-existing. The wellbore may be drilled amongst existing wellbores, for example, as an infill wellbore. A plurality of wellbores (e.g., tens to hundreds of wellbores) are often used in a field to recover the hydrocarbons. As an example, the hydrocarbons may be swept from at least one injection wellbore towards at least one production wellbore and up towards the surface for processing.

The wellbore may have vertical, horizontal, or combination trajectories. For example, the wellbore may be a vertical wellbore, a horizontal wellbore, a multilateral wellbore, an inclined wellbore, a slanted wellbore, etc. The wellbore may include a "build section," which refers to practically any section of a wellbore where the deviation is changing. As an example, the deviation is changing when the wellbore is curving. In a horizontal wellbore, the build section is the curved section between the vertical section of the horizontal wellbore and the horizontal section of the horizontal wellbore. Wellbores that are not horizontal wellbores may include build sections. For example, inclined or slanted wellbores may include a build section.

The wellbore may include a plurality of components, such as, but not limited to, a casing, a liner, a tubing string, a heating element, a sensor, a packer, a screen, a gravel pack, etc. The "casing" refers to a steel pipe cemented in place during the wellbore construction process to stabilize the wellbore. The "liner" refers to any string of casing in which the top does not extend to the surface but instead is suspended from inside the previous casing. The "tubing string" or simply "tubing" is made up of a plurality of tubulars (e.g., tubing, tubing joints, pup joints, etc.) connected together. The tubing string is lowered into the casing or the liner for injecting a fluid into the hydrocarbon-bearing formation, producing a fluid from the hydrocarbon-bearing formation, or any combination thereof. The casing may be cemented in place, with the cement positioned in the annulus between the hydrocarbon-bearing formation and the outside of the casing. The wellbore may also include any completion hardware that is not discussed separately. If the wellbore is drilled offshore, the wellbore may include some of the previous components plus other offshore components, such as a riser.

The wellbore may also include equipment to control fluid flow into the wellbore, control fluid flow out of the wellbore, or any combination thereof. For example, each wellbore may include a wellhead, a BOP, chokes, valves, or other control devices. These control devices may be located on the surface, under the surface (e.g., downhole in the wellbore), or any combination thereof. In some embodiments, the same control devices may be used to control fluid flow into and out of the wellbore. In some embodiments, different control devices may be used to control fluid flow into and out of the wellbore. In some embodiments, the rate of flow of fluids through the wellbore may depend on the fluid handling capacities of the surface facility that is in fluidic communication with the wellbore. The control devices may also be utilized to control the pressure profile of the wellbore.

The equipment to be used in controlling fluid flow into and out of the wellbore may be dependent on the specifics of the wellbore, the hydrocarbon-bearing formation, the surface facility, etc. However, for simplicity, the term "control apparatus" is meant to represent any wellhead(s), BOP(s), choke(s), valve(s), fluid(s), and other equipment and techniques related to controlling fluid flow into and out of the wellbore.

The wellbore may be drilled into the hydrocarbon-bearing formation using practically any drilling technique and equipment known in the art, such as geosteering, directional drilling, etc. Drilling the wellbore may include using a tool, such as a drilling tool that includes a drill bit and a drill string. Drilling fluid, such as drilling mud, may be used while drilling in order to cool the drill tool and remove cuttings. Other tools may also be used while drilling or after drilling, such as measurement-while-drilling (MWD) tools, seismic-while-drilling (SWD) tools, wireline tools, logging-while-drilling (LWD) tools, or other downhole tools. After drilling to a predetermined depth, the drill string and the drill bit are removed, and then the casing, the tubing, etc. may be installed according to the design of the wellbore.

The equipment to be used in drilling the wellbore may be dependent on the design of the wellbore, the hydrocarbon-bearing formation, the hydrocarbons, etc. However, for simplicity, the term "drilling apparatus" is meant to represent any drill bit(s), drill string(s), drilling fluid(s), and other equipment and techniques related to drilling the wellbore.

The term "wellbore" may be used synonymously with the terms "borehole," "well," or "well bore." The term "wellbore" is not limited to any description or configuration described herein.

The term "microemulsion system" as used herein refers to a microemulsion of oil and brine existing as solubilized domains with surfactant occupying the interface between the solubilized domains. The microemulsion system may include more than one surfactant, as well as, co-surfactant, alkali, and/or co-solvent.

Water: The term "water" may be practically any liquid that may be injected into the hydrocarbon-bearing formation. In some embodiments, the water may comprise surface water, water recovered from a production wellbore, brine, sea water, produced formation brine, formation brine, fresh water, produced water, water, saltwater, synthetic brine, synthetic seawater brine, or any combination thereof.

As used in this specification and the following claims, the term "proximate" is defined as "near". If item A is proximate to item B, then item A is near item B. For example, in some embodiments, item A may be in contact with item B. For example, in some embodiments, there may be at least one barrier between item A and item B such that item A and item B are near each other, but not in contact with each other. The barrier may be a fluid barrier, a non-fluid barrier (e.g., a structural barrier), or any combination thereof.

As used in this specification and the following claims, the terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

Unless defined otherwise, all technical and scientific terms used herein have the same meanings as commonly understood by one of skill in the art to which the disclosed invention belongs.

PROCESS OVERVIEW: Various embodiments are provided that allow for simulating fluid flow in a subsurface reservoir and forecasting oil recovery from the subsurface reservoir using a chemical enhanced oil recovery process. In particular, embodiments are provided for simulation of microemulsion systems in chemical enhanced oil recovery processes and eliminating unphysical solutions in chemical enhanced oil recovery simulations produced via calculation of cell surfactant concentration (SC). Moreover, embodiments of recovering hydrocarbons from a hydrocarbon-bearing formation using a chemical enhanced oil recovery process are provided. The chemical enhanced oil recovery process can be carried out in accordance with results from chemical enhanced oil recovery simulations produced via calculation of cell surfactant concentration compared to critical micelle concentration (CMC).

In a first embodiment, the cell surfactant concentration can be calculated via:

$$SC = \frac{V_{surfactant}}{V_{surfactant} + V_{water}} \quad (2)$$

where $V_{surfactant}$ and $V_{water}$ represent volumes of surfactant and water components, respectively. Thus, the cell surfactant concentration (SC) is equivalent to a volume of surfactant component divided by a sum of a volume of surfactant component and a volume of water component.

In a second embodiment, the cell surfactant concentration (SC) can be calculated via:

$$SC = \frac{V_{surfactant}}{V_{water}} \quad (3)$$

where $V_{surfactant}$ and $V_{water}$ represent volumes of surfactant and water components, respectively. Thus, the cell surfactant concentration (SC) is equivalent to a volume of surfactant component divided by a volume of water component.

In the above embodiments, the volume of oil component within a cell is removed from calculation of surfactant concentration, which will be compared with critical micelle concentration (CMC) to determine the appearance and disappearance of the micro-emulsion phase. This prevents the calculated surfactant concentration from dropping below a predetermined threshold value (e.g., a lab measured critical micelle concentration (CMC)) when an oil bank forms near the chemical injection front. For example, a lab measured critical micelle concentration (CMC) can be input into the phase labeling portion of a reservoir simulator as a predetermined threshold value. As such, the lab measured critical micelle concentration (CMC) is input as a constant parameter value (e.g., a value typically between $1.0\times10^{-3}$ and $1.0\times10^{-5}$), and serves as a threshold value in simulation for determining whether grid cells contain a microemulsion (i.e., if the calculated value of surfactant concentration for a particular cell is greater than the lab measured CMC input into the reservoir, then the grid cell is labeled as containing a microemulsion phase for phase behavior calculations). Lab measured critical micelle concentration (CMC) values may be determined, for example, according to the procedures disclosed by L. A. Noll in SPE 21032, titled "The Effect of Temperature, Salinity, and Alcohol on the Critical Micelle Concentration of Surfactants," or by Alhasan B. Fuseni et al. in SPE-188011-MS, titled "Critical Micelle Concentration of Different Classes of EOR Surfactants under Representative Field Conditions."

The above embodiments result in a physical solution for microemulsion phase saturation distribution. Accordingly, the micro-emulsion phase distribution produced by the embodiments of the disclosure exhibit a continuous injection front (i.e., no checkerboard patterns are produced). One skilled in the art will also recognize that since the surfactant component volume is much smaller than the water component volume in chemical enhanced oil recovery processes, Equation 2 and Equation 3 for surfactant concentration typically yield very similar micro-emulsion phase distributions.

Figure 2:
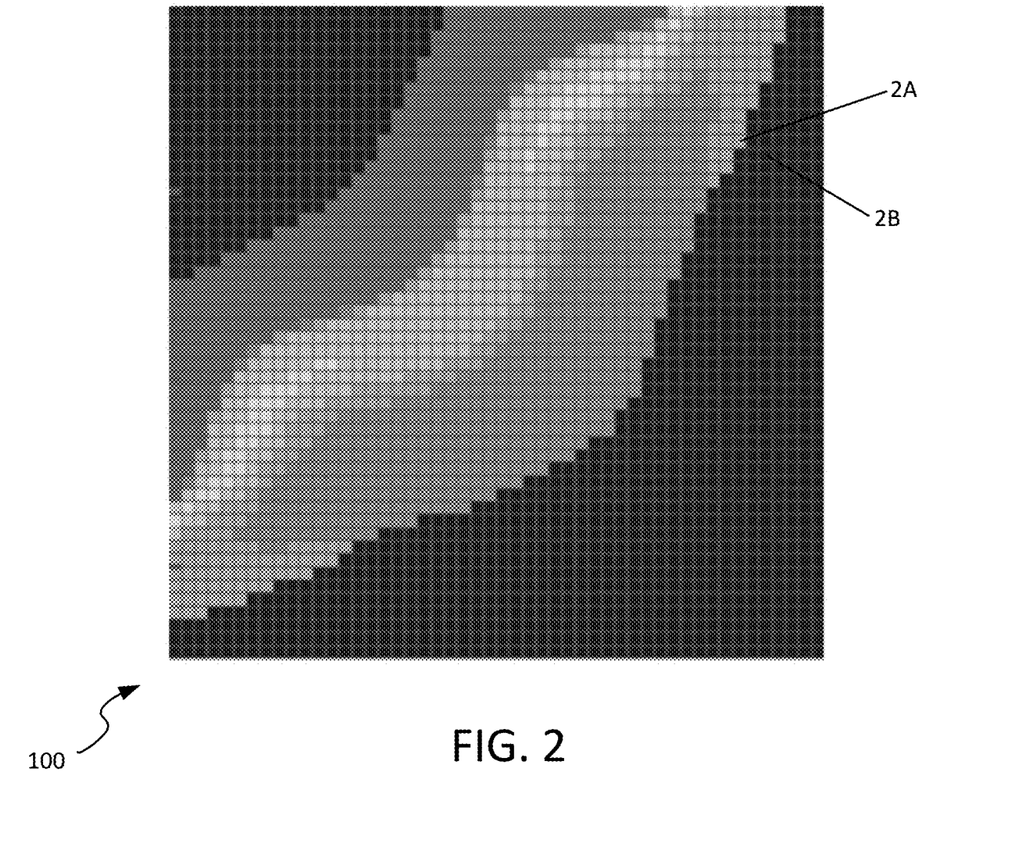
FIG. 2 provides a micro-emulsion phase saturation diagram produced during simulation of a chemical enhanced oil recovery process in a subsurface oil reservoir in accordance with the current disclosure.

FIG. 2 is a diagram showing a user interface 100 displaying micro-emulsion phase saturation from simulation for a chemical injection during an enhanced oil recovery project (e.g., surfactant flooding) according to embodiments of the present disclosure. In FIG. 2, micro-emulsion phase saturation is a physical solution with a continuous injection front (i.e., no checkboard pattern as shown in FIG. 1). In particular, some cells 2A in the simulation grid that are shaded in a lighter color exhibit a microemulsion phase while neighboring or adjacent cells 2B that are shaded in a darker color are shown not having a microemulsion phase. Moreover, proximate the saturation front, no cells 2A containing a microemulsion phase (or a grouping of cells 2A) are surrounded or bordered entirely by cells 2B not having a microemulsion phase.

Figure 3:
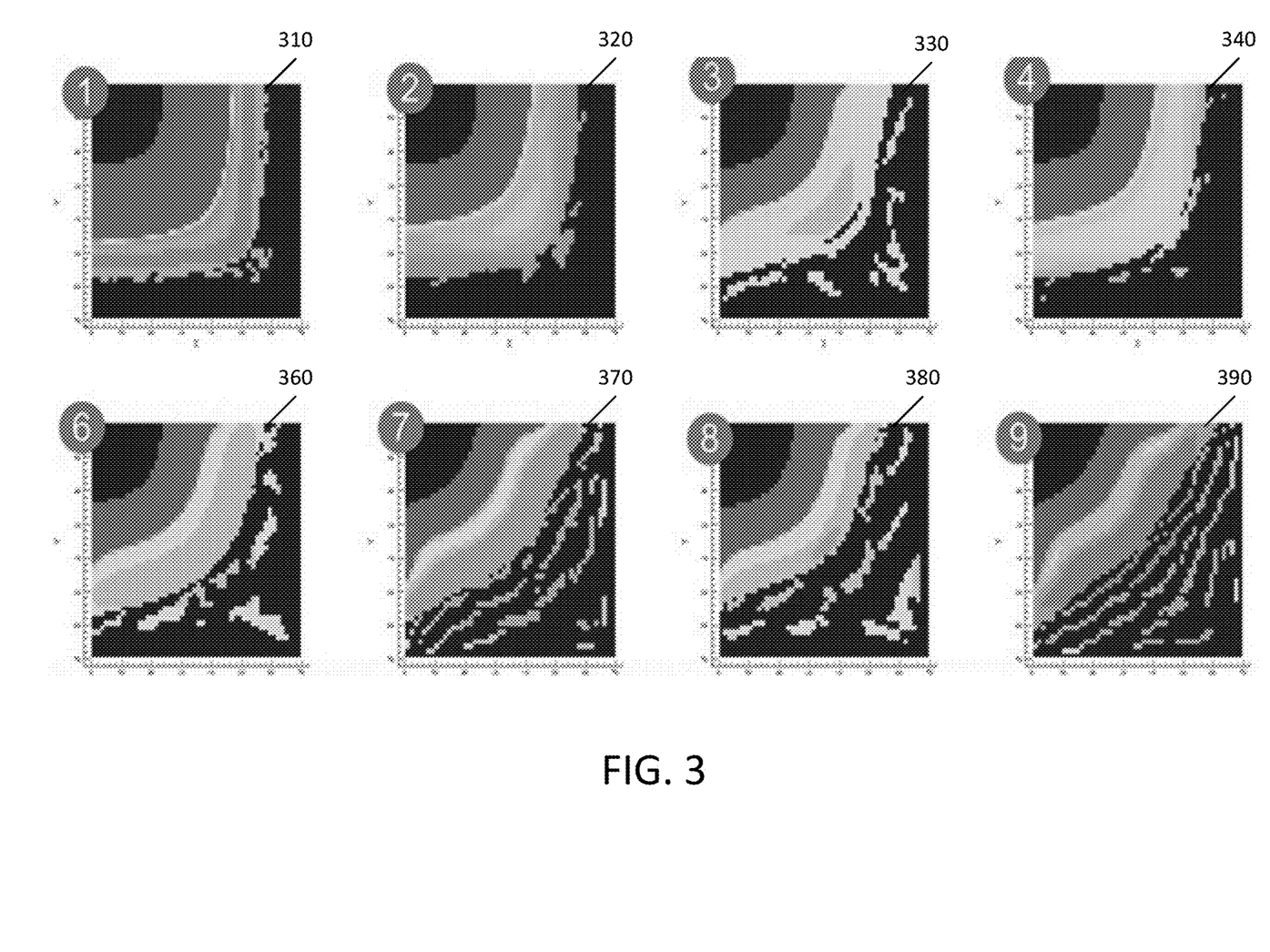
FIG. 3 provides multiple micro-emulsion phase saturation diagrams produced at various time steps in simulation of a chemical enhanced oil recovery process in a subsurface oil reservoir with surfactant injection.
Figure 4:
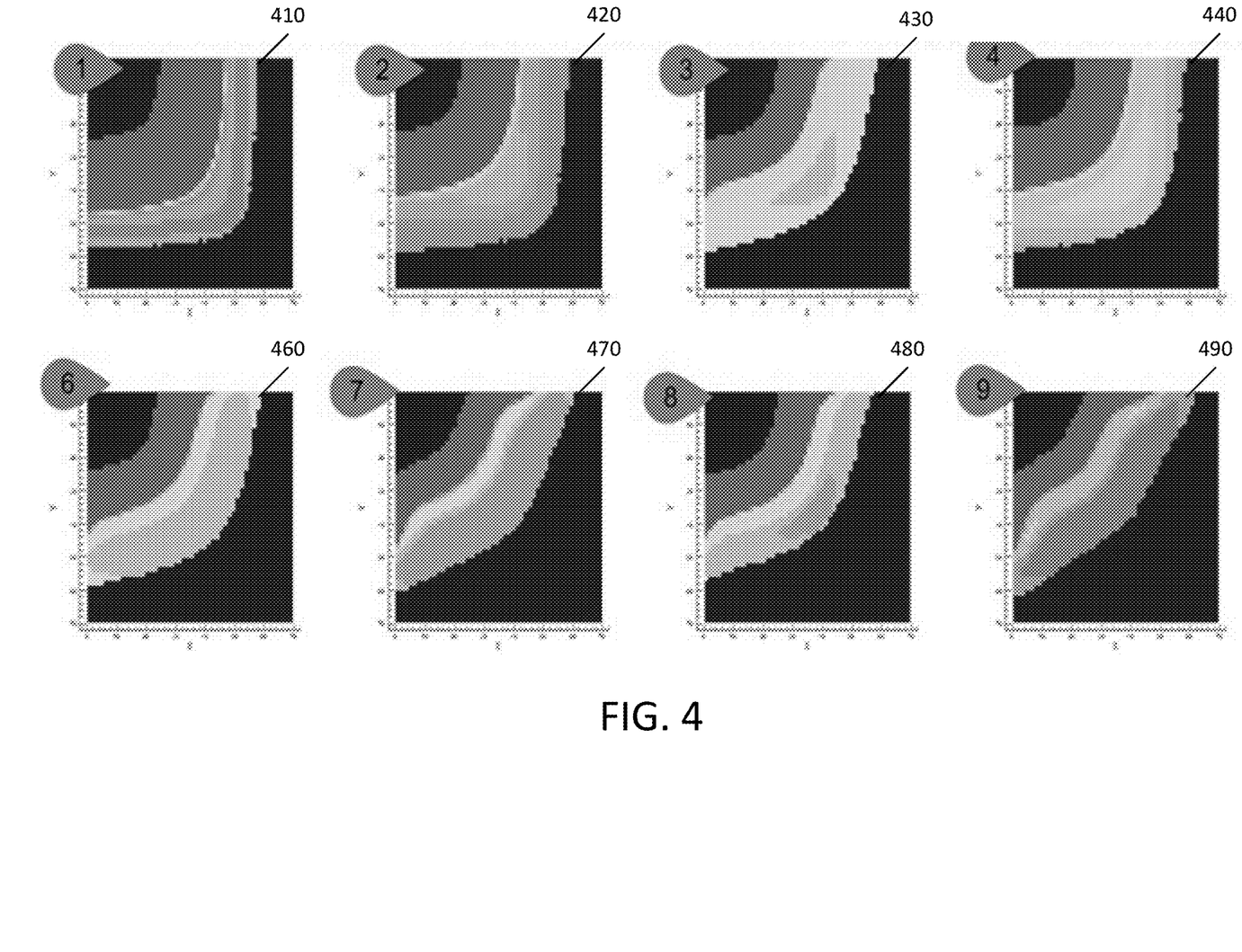
FIG. 4 provides multiple micro-emulsion phase saturation diagrams produced at various time steps in simulation of a chemical enhanced oil recovery process in a subsurface oil reservoir in accordance with the current disclosure.

FIGS. 3 and 4 compare multiple micro-emulsion phase saturation diagrams produced at various time steps (labeled 1-9) in simulation of a chemical enhanced oil recovery process. In particular, the micro-emulsion phase saturation diagrams 310-390 produced in FIG. 3 are generated such that the cell surfactant concentration is determined using Equation 1. Accordingly, checkerboard patterns can be observed at the injection front in various time steps. The micro-emulsion phase saturation diagrams 410-490 produced in FIG. 4 are generated such that the cell surfactant concentration is determined using Equation 2. Accordingly, the solution is physical in nature and no checkerboard patterns are observed at the injection front in the various time steps.

Phase behavior calculations can then be carried out for each of the cells having been identified in a time step as having a microemulsion phase. One skilled in the art, will appreciate that there are many equation-of-state models for computing phase behavior. For example, the Hydrophilic-Lipophilic Difference—Net Average Curvature (HLD-NAC) model for predicting phase behavior was first introduced by Acosta et al., Net-average curvature model for solubilization and supersolubilization in surfactant microemulsions. Langmuir, 19(1), 186-195 (2003). Subsequent models for predicting phase behavior have built upon the HLD-NAC model. These include the HLD-NAC with catastrophe theory model (Jin et al., Physics based HLD-NAC phase behavior model for surfactant/crude oil/brine systems. Journal of Petroleum Science and Engineering, 136, 68-77 (2015)), the HLD-NAC with surfactant continuum model (Nouraei et al., Predicting solubilization features of ternary phase diagrams of fully dilutable lecithin linker microemulsions. Journal of Colloid and Interface Science, 495, 178-190 (2017)), and modified HLD-NAC with characteristic length model (Ghosh et al., Dimensionless Equation of State to Predict Microemulsion Phase Behavior. Langmuir, 32(35), 8969-8979 (2016); Khorsandi et al., Robust Flash Calculation Algorithm for Microemulsion Phase Behavior. Journal of Surfactants and Detergents, 19(6) 1273-1287 (2016)). Additional techniques for predicting solubilization features are described in U.S. patent application Ser. No. 16/128,129, entitled "Method for Predicting Phase Behavior in Chemical Enhanced Oil Recovery Processes" and filed on Sep. 11, 2018, the disclosure of which is hereby incorporated by reference in its entirety.

In some embodiments, the reservoir simulator can be a fully implicit, fully coupled reservoir simulator. Coupling of surfactant phase behavior with hydrocarbon phase behavior can be carried out according to the methods described by Choongyong Han et al. in SPE-182653-MS, titled "A New Four-Phase Flash Algorithm for Surfactant Flood Simulation." Such a flash algorithm can be implemented in chemical flood simulation using the framework disclosed by Xundan Shi et al. in SPE-182703-MS, titled "A Mixed Natural and Concentration Variable Formulation for Chemical Flood Simulation."

Figure 5:
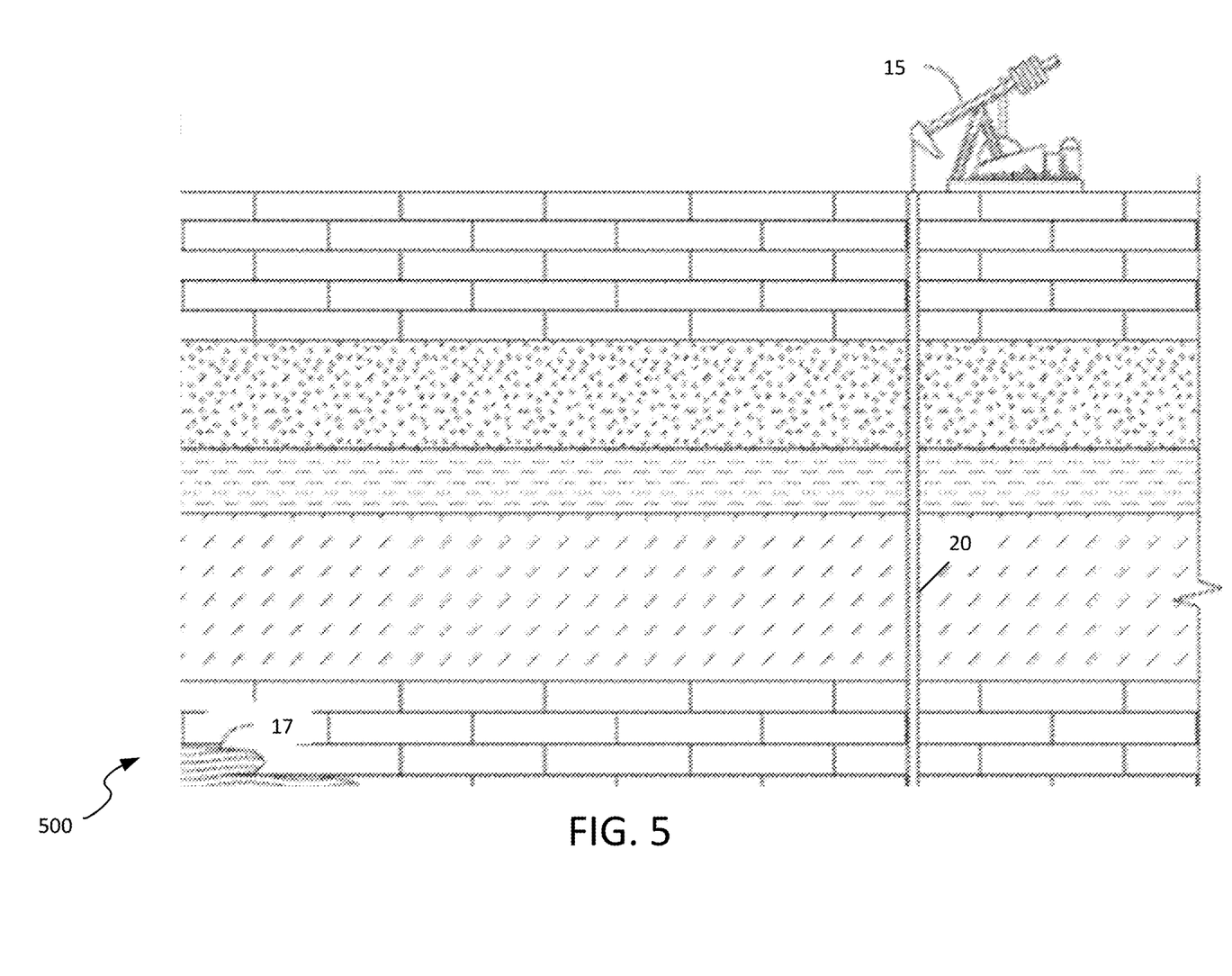
FIG. 5 is a diagram shows a chemical enhanced oil recovery injection into a subsurface oil reservoir.
Figure 6:
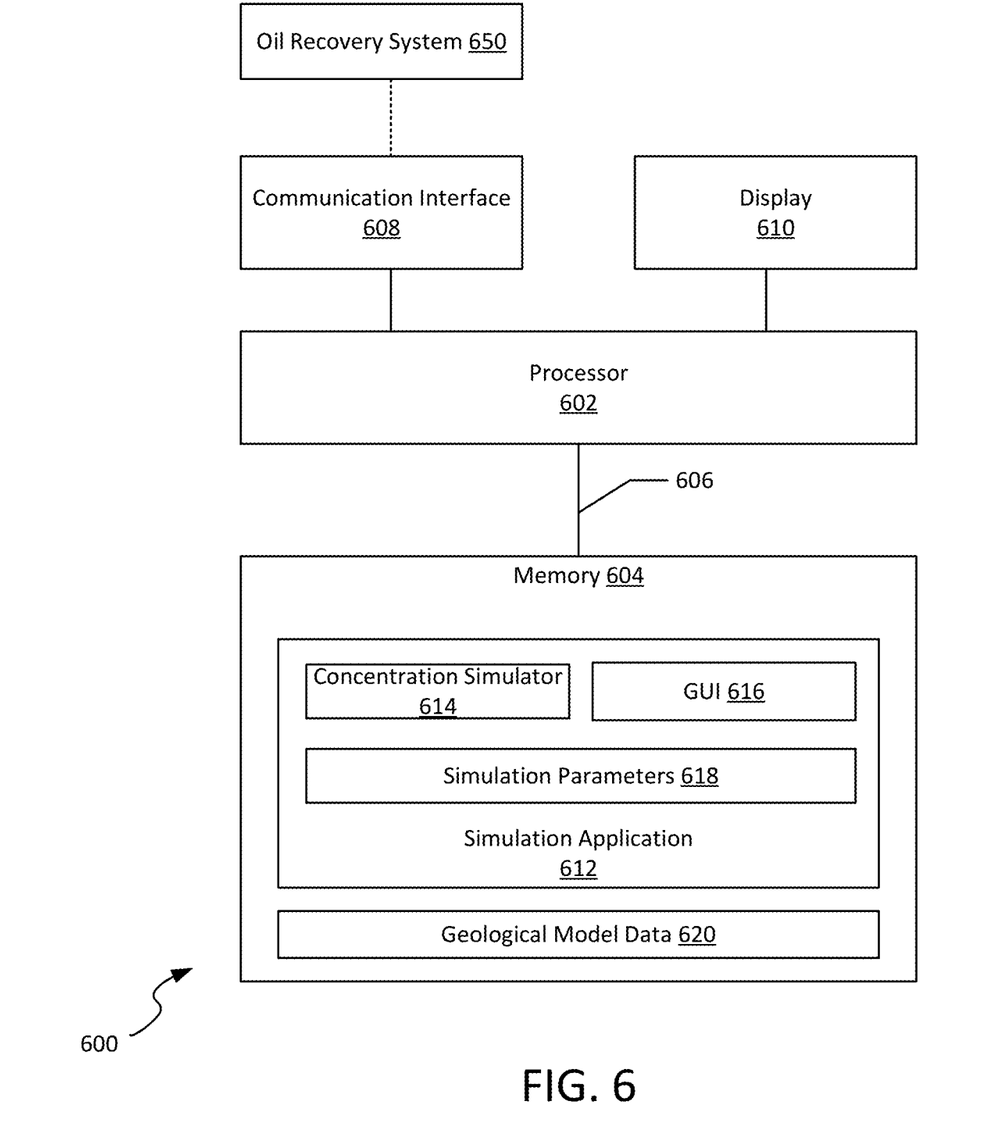
FIG. 6 illustrates an example computing system with which aspects of the present disclosure can be implemented.
Figure 7:
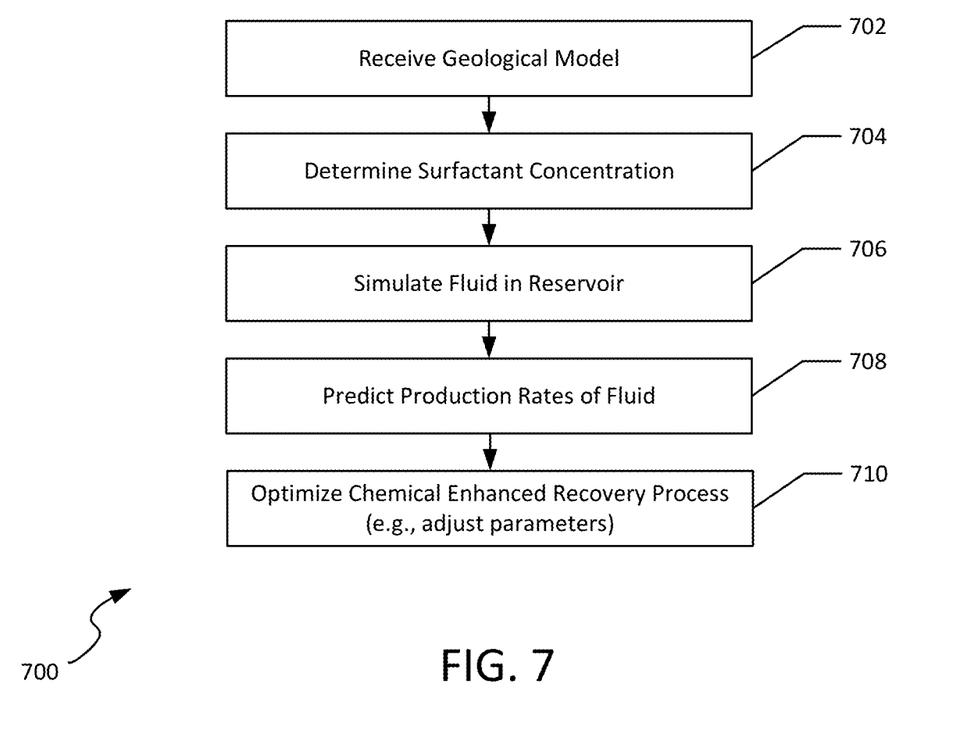
FIG. 7 illustrates a flowchart of a method of simulating a microemulsion system in a chemical enhanced oil recovery process and actions taken in response to such simulation, in an example embodiment.

Referring to FIGS. 5-7, example equipment and techniques for performing the simulation and related hydrocarbon recovery process are shown and described. FIG. 5 illustrates an example structure 500 with which a chemical enhanced oil recovery process can be used. In the example shown, oil recovery equipment 15 is used to establish a well, by forming a wellbore 20 through subsurface materials, to reach an identified oil deposit 17. In example embodiments, the oil recovery equipment can perform a chemical enhanced oil recovery process in which a surfactant is introduced to lower an interfacial tension between oil and water at a subsurface location; additional chemicals or gels can be used for directing flow, adjusting acidity/alkalinity levels, etc. Accordingly, rates and locations of chemical introduction, as well as operational rates of oil recovery equipment (e.g., drill operation rates, rate of introduction of water, pump operation rates, etc.) can be adjusted to change characteristics of such an oil recovery process. As noted above, one or more of these characteristics can be adjusted or set by a user of simulation software that simulates such a chemical-enhanced oil recovery process.

In the example shown, hydrocarbon-bearing formation and the wellbore 20 drilled into the hydrocarbon-bearing formation are in fluid communication (e.g., via perforations), and the injection fluid is injected into the wellbore through a wellhead of the wellbore using at least one pump included in the oil recovery equipment. The hydrocarbons will typically be swept through the hydrocarbon-bearing formation towards at least one production wellbore drilled into the hydrocarbon-bearing formation, enter the at least one production wellbore, and flow up to the surface for processing.

The physical equipment to be used in preparing and injecting the injection fluid is dependent on the specifics of the injection fluid, the specifics of the polymer, the specifics of the injection wellbore(s), specifics of the production wellbore(s), the specifics of the hydrocarbon-bearing formation, etc. However, for simplicity, the term "injection apparatus" is meant to represent any tank(s), mixer(s), pump(s), manifold(s), pipeline(s), valve(s), fluid(s), polymer (s), and other equipment and techniques related to preparing the injection fluid comprising the polymer and injecting the injection fluid. The "injection apparatus" may even be utilized for another injection in some embodiments, not just the in the context of the CEOR process.

Referring to FIG. 6, details regarding a computing system 600 useable to perform the simulations described herein is disclosed. The computing system 600 can be used, for example, to perform methods of simulation of a chemical enhanced oil recovery process such as is described above, as well as the methods of simulation and management of such a process as described below in connection with FIG. 7.

In general, the computing system 600 includes a processor 602 communicatively connected to a memory 604 via a data bus 606. The processor 602 can be any of a variety of types of programmable circuits capable of executing computer-readable instructions to perform various tasks, such as mathematical and communication tasks.

The memory 604 can include any of a variety of memory devices, such as using various types of computer-readable or computer storage media. A computer storage medium or computer-readable medium may be any medium that can contain or store the program for use by or in connection with the instruction execution system, apparatus, or device. By way of example, computer storage media may include dynamic random access memory (DRAM) or variants thereof, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally includes at least one or more tangible media or devices. Computer storage media can, in some embodiments, include embodiments including entirely non-transitory components. In the embodiment shown, the memory 604 stores a simulation application 612, discussed in further detail below. The computing system 600 can also include a communication interface 608 configured to receive and transmit data, for example to access data in an external database. Additionally, a display 610 can be used for viewing simulation results generated by the simulation application 612.

In various embodiments, the simulation application 612 allows a user to simulate reactions within a volume during a chemical enhanced oil recovery process. As noted above, the simulation application can be a fully implicit, fully coupled reservoir simulator. The simulation application 612 includes a simulator 614, a graphical user interface (GUI) generator 616, and stores a plurality of operational simulation parameters 618. The concentration simulator 614 is configured to receive data for simulation, such as geological model data 620 stored in the memory 604. The concentration simulator 614 uses simulation parameters (e.g., rates of introduction of water and surfactant or other chemicals, rates of operation of machinery, etc.) in combination with the geological model data 620 to simulate, for each of a plurality of cells within a volume, the cell surfactant concentration. The GUI generator 616 can display that information in graphical form to a user via the display 610; example user interface outputs are as shown in FIGS. 2 and 4. Additional details regarding such components are provided below in greater detail in connection with the execution of corresponding method steps as illustrated in FIG. 7.

In example embodiments, the computing system 600 can be interfaced to a remote system for purposes of receiving operational data and outputting changes to that remote system, e.g., for purposes of setting parameters in such a system. In the example shown, the computing system 600 is connected, via communication interface 608, to an oil recovery system 650. The oil recovery system 650 can be a system used to perform a chemical enhanced oil recovery process. The oil recovery system 650 can, in various embodiments, provide information to the computing system 600, such as information about a geological model or equipment used. The system 600 can provide to the oil recovery system 650 one or more operational parameters that are determined based on execution of the simulation application 612. The operational parameters may be based on an optimization performed using the simulation application 612, and may be provided to the oil recovery system 650 either before initiation of an oil recovery process (e.g., in the case a simulation is performed prior to initiation of oil recovery) or during such an oil recovery process to adjust parameters in response to concurrent simulation of the process.

FIG. 7 illustrates an example flowchart of a method 700 of simulating and managing a chemical enhanced oil recovery process, according to an example embodiment. In the example shown, the method 300 operates on a computing system, such as system 600 of FIG. 6.

In the example shown, the method includes receiving a geological model of an area of interest (step 702). The area of interest can be, for example, an area where a chemical-enhanced oil recovery process is to be performed. The area may include, for example, a stratigraphic model including an area or concentration of oil to be recovered. The area is then segmented by the computing system into a plurality of cells, within each of which a surfactant concentration can be determined in accordance with the present disclosure.

In the example shown, the method 700 includes determining a surfactant concentration within each cell of the area of interest (step 704). Determining the surfactant concentration can be based, for example, on a volume of water and a volume of surfactant within the cell, and independently of a volume of oil in that cell, as discussed above. In example embodiments, only volume of water and volume of surfactant are used, such as is illustrated in Equations 2-3, above.

Still further, the method 700 includes simulating fluids within the reservoir (step 706). This can include simulation of fluids flowing within the reservoir by modeling introduction of water and/or surfactant over time and modeling flow of all fluids within the reservoir at a plurality of sequential times, as illustrated in FIG. 4, above. Based on the simulation of fluid flow, production rates of fluid, such as oil, can be predicted (step 708). Simulation of fluid within the reservoir, as well as prediction of production rates, can include generating a user interface displaying fluid flow simulations and production rates over time. Accordingly, since the user interface is generated based on improved simulation parameters, the simulation user interface generated has improved accuracy (i.e., is more closely tied to the actual physical reaction that occurs).

In example embodiments simulation of fluid within the reservoir, and generation of the user interface, can include display of one or more user-selectable or user-editable parameters for performing a chemical enhanced oil recovery process. For example, in various embodiments, the visual representation includes at least one of: a location of at least one injection wellbore, a location of at least one production wellbore, a composition of an injection fluid to be injected into at least one injection wellbore, and an injection rate of at least one injection wellbore. Other types of features may be added to or edited within the user interface as well.

Based on the simulation performed, the method 700 can also be used to optimize the chemical enhanced oil recovery process (step 710). This can include, for example, adjusting one or more recovery process parameters (e.g., simulation parameters 618) or automatically recommending adjustment of one or more recovery process parameters to improve the oil recovery process (e.g., to improve overall recovery, recovery rate, chemical usage, etc.). Still further optimizing the chemical enhanced oil recovery process can include directing and controlling various operations to be performed on a site corresponding to the simulated site. Such operations can include selection of a certain injection wellbore, steering a drilling tool (including a drill bit), and performing geosteering to locate the well based on a particular field development plan. Such operations may be selected based on performance of one or more simulations and selection of a particular desirable simulation.

Additionally, based on the simulation performed, the method 700 can further include directing and controlling the actions of another entity to accomplish at least one of the inventive concepts, including, for example, drilling of an injection wellbore in response to simulating of fluid flow, directing addition of components to injection fluid in response to simulated fluid flow, directing establishment of an injection rate in response to the simulated fluid flow, and/or directing adjustment of an injection rate in response to the simulated fluid flow. Other operations, or directed operations, could be performed/directed as well.

Referring to FIG. 7 generally, it is noted that although the specific steps of method 700 are shown in a particular order, no order is implied as required. As noted above, the simulation methodology may be performed before, during, or after a chemically enhanced oil recovery process, and the various steps included in simulation may be performed one or more times for improved simulation, particularly where a simulation will be performed over a predetermined amount of time (e.g., to show time iterations of the simulation). Accordingly, the specific ordering of steps noted above is not intended to be limited to that shown in FIG. 7. In example applications, the simulations performed herein can be performed a number of times using different injection rates, compositions of injection fluid, and other factors to determine an optimal efficiency. Examples of such techniques are described in the following papers:

Babakhani Dehkordi P (2018) A Field Scale Simulation Study of Surfactant and Polymer Flooding in Sandstone Heterogeneous Reservoir. J Pet Environ Biotechnol 9: 366.

H. Pu & D. Yin (2009) A Numerical Simulation Study on Surfactant Flooding and Its Field Application in Daqing's Pilot Test, Petroleum Science and Technology, 27:5, 474-485

Feng Xu et al., (2011) Case Study: Numerical Simulation of Surfactant Flooding in Low Permeability Oil Field, Soc. Of Petrol. Eng. SPE145036.

As reflected in FIGS. 6-7, above, embodiments of the present disclosure can be implemented as a computer process (method), a computing system, or as an article of manufacture, such as a computer program product or computer readable media. The computer program product may be a computer storage media readable by a computer system and encoding a computer program of instructions for executing a computer process. Accordingly, embodiments of the present disclosure may be embodied in hardware and/or in software (including firmware, resident software, microcode, etc.). In other words, embodiments of the present disclosure may take the form of a computer program product on a computer-usable or computer-readable storage medium having computer-usable or computer-readable program code embodied in the medium for use by or in connection with an instruction execution system.

In operation, system information can be input through the reservoir simulator, e.g., the simulation application 612 of FIG. 6. For example, a person is capable of interacting with the system such as through a keyboard, mouse, touch-screen display, or voice-command controls. Operator-entered data (e.g., user-defined parameters such as a lab measured value for CMC), or any information generated by system (e.g., system generated computed solutions), can be stored in one or more data files. The system can also include a visual display or reporting unit. For example, the output from simulations can be transformed into image data representations for display to a user or operator. Accordingly, "producing a visual display" or "display" or "displaying" includes any direct or indirect acts (electronically or physically) to report information or outputs of the system. The displayed information can be utilized to forecast or optimize the production performance of the subterranean reservoir, to enhance surface facilities, or used in making other reservoir management decisions.

In some instances, a desirable simulation may be selected by the computing system itself (e.g., the simulation application 612) by applying a machine learning algorithm and/or one or more artificial intelligence features to a particular dataset, and optionally allowing the computing system to select a particular simulation and set of optimal parameters or to suggest via the user interface one or more operational parameters that could be used or optimized in a chemical enhanced oil recovery process.

The term "optimize" (as well as derivatives, other forms of this term, and linguistically related words and phrases), as used herein, are not intended to be limiting in the sense of requiring the present invention to find the best mathematical solution or to make the best decision. Rather, the terms can describe working towards a solution which may be the best available solution, a preferred solution, or a solution that offers a specific benefit within a range of constraints; or continually improving; or refining; or searching for a high point or a maximum for an objective; or processing to reduce a penalty function.

The computer program product can be stored on a non-transitory computer usable or processor readable medium, which can be executed by one or more processors of the controller. Current examples of such non-transitory medium include, but are not limited to, read-only memory (ROM) devices, random access memory (RAM) devices and semiconductor-based memory devices. This includes flash memory devices, programmable ROM (PROM) devices, erasable programmable ROM (EPROM) devices, electrically erasable programmable ROM (EEPROM) devices, dynamic RAM (DRAM) devices, static RAM (SRAM) devices, magnetic storage devices (e.g., floppy disks, hard disks), optical disks (e.g., compact disks (CD-ROMs)), and integrated circuits. Non-transitory medium can be transportable such that the one or more computer programs (i.e., a plurality of instructions) stored thereon can be loaded onto a computer resource (e.g., the controller) such that when executed, performs the aforementioned functions of the various embodiments of the present invention.

Communication between any components of system can be transferred over a communications network. Communications network can be any means that allows for information transfer to facilitate sharing of knowledge and resources, and can utilize any communications protocol such as the Transmission Control Protocol/Internet Protocol (TCP/IP). Examples of communications networks include, but are not limited to, personal area networks (PANs), local area networks (LANs), wide area networks (WANs), campus area networks (CANs), and virtual private networks (VPNs). Communications network can also include any hardware technology or equipment used to connect individual devices in the network, such as by wired technologies (e.g., twisted pair cables, co-axial cables, optical cables) or wireless technologies (e.g., radio waves).

As one skilled in the art will appreciate, the results obtained from using embodiments described herein can be used to make equipment improvements, such as to surface facilities, or for determining where to drill additional wells for increasing production. Injection and production flow rates can also be optimized, such as by altering various flow control devices (e.g., chokes or orifices). This can also impact relative rates at which oil, water and gas are produced from each wellbore. Any physical action associated with pattern balancing through injection and production rate allocation, locating and producing by-passed oil pockets, and tracking fluid displacements (in production, injection, or storage) can also be performed. Accordingly, each of these variables can be used in the simulation parameters that are accounted for by the computing system and/or output to an oil recovery system. For example, reservoir simulation can be used to maximize the net-present-value (NPV), or some other metric, from the hydrocarbon recovery and the development cost by selecting the recovery scheme, identifying the optimum number of wells and their locations, and predicting the production rates of oil, gas, and water. Improvement in simulation models is therefore crucial for more accurate investment decisions.

The present disclosure provides a complete description of the methods and systems. Since many embodiments of the methods and systems can be made without departing from the spirit and scope of the invention, the invention resides in the claims hereinafter appended.

REFERENCES CITED

All references cited herein are incorporated herein by reference in their entirety and for all purposes to the same extent as if each individual publication or patent or patent application was specifically and individually indicated to be incorporated by reference in its entirety herein for all purposes. Discussion or citation of a reference herein will not be construed as an admission that such reference is prior art to the present invention.

Modifications

Many modifications and variations of this invention can be made without departing from its spirit and scope, as will be apparent to those skilled in the art. The specific embodiments described herein are offered by way of example only, and the invention is to be limited only by the terms of the claims, along with the full scope of equivalents to which such claims are entitled.

The invention claimed is:

1. A method for optimizing a chemical enhanced oil recovery process for a subsurface reservoir, the method comprising:
   receiving a geological model of a subsurface reservoir, the geological model defining a grid having a plurality of cells;
   determining a surfactant concentration for each cell based on a volume of surfactant and a volume of water within the cell and independently from a volume of oil within the cell;
   based on the determined surfactant concentration, selecting operational parameters for the surfactant concentration for directing a fluid flow simulation;
   based on the selected operational parameters, simulating fluids flowing within the subsurface reservoir over time, including varying parameters for a plurality of scenarios;
   based on the simulation of fluids flowing within the subsurface reservoir, predicting production rates of flow of the fluids for the plurality of the scenarios; and
   optimizing a chemical enhanced recovery process for the subsurface reservoir, including displaying production rates over time, based on the predicted production rates of flow of the fluids.

2. The method of claim 1, wherein the surfactant concentration for each cell is determined as a function of the volume of surfactant and the volume of water within the cell.

3. The method of claim 1, further comprising comparing the surfactant concentration for each cell with a predetermined threshold value to determine whether each cell contains a microemulsion.

4. The method of claim 3, wherein the predetermined threshold value comprises a critical micelle concentration determined based on laboratory experiments.

5. The method of claim 4, further comprising optimizing the chemical enhanced recovery process in the subsurface reservoir based on results from the simulation of fluids flowing within the subsurface reservoir using the critical micelle concentration.

6. The method of claim 1, further comprising selecting operational parameters for salinity concentration for directing the fluid flow simulation.

7. The method of claim 1, wherein the simulated fluids flowing in the subsurface reservoir comprises one or more of water, brine, surfactant, oil, co-surfactants, alkali, cosolvents, and polymer.

8. The method of claim 1, wherein selecting operational parameters is performed by applying a machine learning algorithm.

9. The method of claim 1, wherein determining the surfactant concentration for each cell is based only on a volume of surfactant and a volume of water within the cell.

10. The method of claim 1, wherein simulating fluids flowing in the subsurface reservoir comprises generating a visual representation of the plurality of cells, the visual representation eliminating one or more simulation artifacts that represent unphysical solutions occurring during simulation of the chemical enhanced oil recovery process and the visual representation includes at least one of: a location of at least one injection wellbore, a location of at least one production wellbore, a composition of an injection fluid to be injected into at least one injection wellbore, and an injection rate of at least one injection wellbore.

11. The method of claim 1, further comprising, in response to the simulated flow of fluids flowing within the subsurface reservoir, adjusting one or more oil recovery parameters used in performing the chemical enhanced oil recovery process.

12. The method of claim 1, further comprising generating a user interface displaying the fluid flow simulations and the production rates over time.

13. A system for optimizing a chemical enhanced oil recovery process, comprising:
   a memory communicatively connected to a processing unit, the memory storing instructions which, when executed by the processing unit, cause the system to simulate a microemulsion system in a chemical enhanced oil recovery process, the instructions causing the processing unit to perform:
      receiving a geological model of a subsurface reservoir, the geological model defining a grid having a plurality of cells;
      determining a surfactant concentration for each cell based on a volume of surfactant and a volume of water within the cell and independently from a volume of oil within the cell;
      based on the determined surfactant concentration, selecting operational parameters for the surfactant concentration for directing a fluid flow simulation;
      based on the selected operational parameters, simulating fluids flowing within the subsurface reservoir over time, including varying parameters for a plurality of scenarios;

based on the simulation of fluids flowing within the subsurface reservoir, predicting production rates of flow of the fluids for the plurality of the scenarios; and optimizing a chemical enhanced recovery process for the subsurface reservoir, including displaying production rates over time, based on the predicted production rates of flow of the fluids.

14. The system of claim 13, wherein the surfactant concentration for each cell is determined as a direct function of the volume of surfactant and the volume of water within the cell.

15. The system of claim 13, wherein determining the surfactant concentration for each cell is based only on a volume of surfactant and a volume of water within the cell.

16. The system of claim 13, wherein simulating fluids flowing in the subsurface reservoir comprises generating a visual representation of the plurality of cells, the visual representation eliminating one or more simulation artifacts that represent unphysical solutions occurring during simulation of the chemical enhanced oil recovery process.

17. The system of claim 13, further comprising, in response to the simulated fluid flow, outputting from the system one or more adjusted oil recovery parameters used in performing the chemical enhanced oil recovery process.

18. The system of claim 17, wherein the system comprises a plurality of computing systems communicatively connected to a control system for controlling the chemical enhanced oil recovery process, and wherein outputting from the system the one or more adjusted oil recovery parameters comprises automatically transmitting the one or more adjusted oil recovery parameters to the control system.

19. The system of claim 13, further comprising a user interface displaying the fluid flow simulations and the production rates over time.

20. A non-transitory computer-readable storage medium including computer-readable instructions, which when executed by a processor is operative to:

receive a geological model of a subsurface reservoir, the geological model defining a grid having a plurality of cells;

determine a surfactant concentration for each cell based on a volume of surfactant and a volume of water within the cell and independently from a volume of oil within the cell;

based on the determined surfactant concentration, selecting operational parameters for the surfactant for directing a fluid flow simulation;

based on the selected operational parameters, simulate fluids flowing within the subsurface reservoir over time, including varying parameters for a plurality of scenarios:

based on the simulation of fluids flowing within the subsurface reservoir, predict production rates of flow of the fluids for the plurality of the scenarios; and optimize a chemical enhanced recovery process for the subsurface reservoir, including display production rates over time, based on the predicted production rates of flow of the fluids.

* * * * *